(12) United States Patent
Roux Dit Buisson

(10) Patent No.: US 9,045,724 B2
(45) Date of Patent: Jun. 2, 2015

(54) CONTINUOUS OR SEMI-CONTINUOUS FLOW PHOTOBIOREACTOR AND METHOD OF USE

(76) Inventor: Jean-Louis Roux Dit Buisson, Gockhausen (CH)

( * ) Notice: Subject to any disclaimer, the term of this patent is extended or adjusted under 35 U.S.C. 154(b) by 0 days.

(21) Appl. No.: 13/702,100

(22) PCT Filed: Jun. 6, 2011

(86) PCT No.: PCT/IB2011/052457
§ 371 (c)(1),
(2), (4) Date: Dec. 5, 2012

(87) PCT Pub. No.: WO2011/154886
PCT Pub. Date: Dec. 15, 2011

(65) Prior Publication Data
US 2013/0078708 A1    Mar. 28, 2013

(30) Foreign Application Priority Data
Jun. 7, 2010   (CH) ........................... 0903/10

(51) Int. Cl.
*C12M 3/00*   (2006.01)
*C12M 1/00*   (2006.01)
*C12M 1/06*   (2006.01)
*C12M 1/26*   (2006.01)
*C12M 1/34*   (2006.01)

(52) U.S. Cl.
CPC .............. *C12M 31/10* (2013.01); *C12M 21/02* (2013.01); *C12M 27/08* (2013.01); *C12M 31/12* (2013.01); *C12M 33/00* (2013.01); *C12M 41/12* (2013.01); *C12M 41/06* (2013.01)

(58) Field of Classification Search
CPC ....... C12M 21/02; C12M 31/10; C12M 31/02; C12M 31/08; C12M 23/06; A01G 33/00; C12N 1/12
USPC .............. 435/257.1, 286.1, 292.1; 362/249.1; 47/1.4
See application file for complete search history.

(56) References Cited

U.S. PATENT DOCUMENTS

| 2,815,607 | A | 12/1957 | Schroeder et al. |
| 3,520,081 | A | 7/1970 | Oswald et al. |

(Continued)

FOREIGN PATENT DOCUMENTS

| JP | 4084883 | 3/1992 |
| WO | WO 86/05202 | 9/1986 |
| WO | WO 2009/142765 | 11/2009 |

OTHER PUBLICATIONS

Written Opinion in International Application No. PCT/IB2011/052457, Sep. 22, 2011, pp. 1-4.

(Continued)

*Primary Examiner* — Michael Hobbs
(74) *Attorney, Agent, or Firm* — Saliwanchik, Lloyd & Eisenschenk

(57) ABSTRACT

The present invention is directed to a photobioreactor for continuous or semi-continuous flow culturing photosynthesizing biomass and related method. In particular, the invention relates to a photobioreactor for continuous or semi-continuous flow culturing photosynthesizing algal biomass and related method. The photobioreactor comprises a gas feeding portion (60), a biomass-directing flow propulsion device (47) on a lighting system (5).

17 Claims, 8 Drawing Sheets

(56) References Cited

U.S. PATENT DOCUMENTS

| | | |
|---|---|---|
| 5,958,761 A | 9/1999 | Yogev et al. |
| 6,579,714 B1 | 6/2003 | Hirabayashi et al. |
| 2009/0029445 A1 | 1/2009 | Eckelberry et al. |
| 2009/0148931 A1* | 6/2009 | Wilkerson et al. ......... 435/286.1 |
| 2009/0178495 A1* | 7/2009 | Steigmiller et al. ....... 73/863.72 |
| 2009/0291485 A1 | 11/2009 | Shigematsu et al. |
| 2010/0005711 A1 | 1/2010 | McNeff |
| 2010/0034050 A1 | 2/2010 | Erb et al. |

OTHER PUBLICATIONS

Chisti, Y. "Biodiesel from microalgae" *Biotechnology Advances*, 2007, pp. 294-306, vol. 25.

Gudin, C. et al. "Bioconversation of Solar Energy Into Organic Chemicals by Microalgae" *Advances in Biotechnological Processes*, 1986, pp. 73-109, vol. 6.

Arino, J. "Modélisation structurée de la croissance du phytoplancton en chemostat" *Université J Fourrier, Thesis*, Jan. 12, 2001, pp. 1-154.

* cited by examiner

B

C

CONTINUOUS OR SEMI-CONTINUOUS FLOW PHOTOBIOREACTOR AND METHOD OF USE

This application is the U.S. national stage application of International Patent Application No. PCT/IB2011/052457, filed Jun. 6, 2011.

FIELD OF THE INVENTION

The present invention relates to a photobioreactor for culturing biomass, especially photosynthesizing algal biomass.

BACKGROUND OF THE INVENTION

A worldwide concern for increasing global levels of carbon dioxide ($CO_2$) in the atmosphere has emerged in the last ten years. Countries and governments are continuously trying to implement regulatory frameworks in order to incite efforts for reducing the overall emissions of $CO_2$ and/or equivalent greenhouse gases. Biological carbon sequestration though photosynthesis is a natural way to recycle carbon that has been recently extensively explored for addressing this problem.

Further, worldwide fossil fuel deposit depletion has pushed researching for alternatives to products that are currently processed from petroleum. In certain applications where high amounts of fuels are needed remotely from sources of supply (e.g. forward military bases or remote exploratory camps experience), costs associated with conventional fuels are high, primarily due to expenses involved in fuel delivery and associated pollution due to transportation means. Therefore, alternatives to produce fuels at the point of use, rather than transporting them to the desired site have been investigated to reduce those costs. In this effort, biofuels such as biodiesel have been identified as a possible alternative for replacing fossil fuel consumption without increasing the $CO_2$ content of the atmosphere. However, the process involved in creating biofuel from biomass is expensive relative to the process of extracting and refining petroleum.

A number of strategies are focused on methods to increase carbon dioxide uptake in biological systems such as green plants through sunlight and $CO_2$ uptake while research went on for optimizing production yields, diversifying and valorising the biomass by-products resulting from photosynthesis. However, the industrial development of those strategies has been hampered by many difficulties in transposing those experimental methods into scalable and/or cost effective solutions. In particular, control of the main parameters affecting the rate of photosynthesis, e.g. a favorable temperature, intensity and wavelength of light, and availability of nutrients such as carbon dioxide has proven to be delicate for closed system applications (e.g. photobioreactors), whereas open ponds to grow biomass suffer from risks of contamination and exhibit high operating costs.

Among phototrophic microorganisms, microalgae is one of the most efficient organisms for converting solar energy using carbon dioxide as growth nutrient and is an efficient producer of oxygen and biomass. Valuable components such as carbohydrates, sugars, proteins and fat can be harvested from the biomass and directly or indirectly converted into high value added products such as pharmaceutical products, nutraceutials, cosmetic products, food products, fine chemicals usually synthesized in chemical plants, or energy supplies such as methane or more interestingly biodiesel and other fuels used in turbines and/or thermal cycle engines for generating movement, in transportation, essentially.

It is known that microalgae productivity is limited by three major factors: availability of light and nutrients, and temperature. Historically, most efforts have been invested in developing the optimum nutrients for any specific microalgae, notably by saturating the photosynthesizing system with $CO_2$. Land-based (e.g. ponds) microalgae culture plants, while showing some effectiveness in capturing $CO_2$, are limited by available land space, water supplies (mainly due to evaporation), external contamination (e.g. other species, bird dejections), productivity (not operable at night) and costs associated with the processing of huge quantities of water. Optimal temperature conditions for efficient biomass production are usually selected in accordance with the climatic conditions prevailing in a chosen site. Yet, even in such sites, winter and night temperatures, as well as morning hour temperatures pose serious limitations to growth rates.

Further, UV exposure of the microalgal culture in outdoors production plants results in the oxidation of the microalgae at the surface of the water. Attempts to solve these problems led to the creation of shallow ponds or raceways. However, such shallow water approaches engender high evaporation and saline deposits, which also reduce the efficacy of continuous outdoor growth. Overall, weather, diurnal cycles, invasion by opportunistic species and external pollutions further aggravate the difficulties of mass microalgae culturing in outdoor settings.

Photobioreactors (PBRs) for photosynthesizing biomass culture provide a compact infrastructure designed to address the above problems. The scale-up of photobioreactors to achieve a commercially viable production of algae products is hampered by the limitation of available lighting, both in terms of light delivery and distribution and of energy expenditure. For instance, current methods of mass cultivation of marine algae include translucent fiberglass cylinders, polyethylene bags, carboys and tanks under artificial lighting or natural illumination in greenhouses. During the microalgae growing process the organisms multiply and the culture density increases, and light ends up not being able to penetrate below a few centimeters of depth below the surface of the algae culture thereby decreasing the volumetric productivity of the system.

U.S. Pat. No. 3,520,081 discloses a rotating tank that enhances contact between microalgae and light to accelerate microalgae growth. While such rotating tanks have some benefits, the impracticality of scale becomes apparent when addressing very large scale systems, e.g., multi million gallon systems. U.S. Pat. No. 6,579,714 describes a microalgae culture apparatus and method utilizing a growth apparatus having spaced apart inner and outer walls which are dome-shaped, conical, or cylindrical. Light can pass through the walls into the space between where the algae are cultured. U.S. Pat. No. 5,958,761 describes a tubular bioreactor including a tubular housing surrounding a tubular envelope made in a translucent material and defining a space there between to be filled with a fluid of selective refractive index and the radiation concentration power into the reactor is controlled by modifying the refractive index of the fluid. U.S. 2009/0029445 discloses a biological growth reactor comprising a mixer, a mixing chamber and a reaction chamber comprising a light distributing and fluid dispensing rod. U.S. 2009/0291485 discloses a culture system comprising a culture tank, a rotatable light array and a rotational drive.

However, in current PBRs, the costs in lighting and energy requirements have made prior solutions impractical for all but the culturing of organisms used in high value products such as pharmaceuticals, cosmetics, food products and/or neutraceuticals. Therefore, in spite of higher yields in microalgae culture obtained in some tightly controlled laboratory experiments, heretofore, efforts at microalgal mass culture have been disappointing in that they were inefficient and uneconomical and in particular current microalgae processing methods have failed to result in cost effective microalgae-derived biofuels.

SUMMARY OF THE INVENTION

It is an object of this invention to provide a photobioreactor for culturing and processing photosynthesizing biomass, especially microalgae biomass, that may be operated in continuous or semi-continuous flow, allows high biomass production yields (e.g. per unit of time, of volume and of footprint surface area) and that provides for effective scaling-up of production units.

Objects of this invention have been achieved by providing a photobioreactor.

Disclosed herein is a photobioreactor for continuous or semi-continuous flow culturing photosynthesizing biomass, the photobioreactor including a housing defining an interior chamber comprising a culture chamber portion and a gas feeding chamber portion; a temperature regulation system; a flow-regulating system comprising a culture mixing and concentrating entity comprising a biomass-directing flow propulsion device; and a lighting system, the culture chamber portion comprising a culture concentrating zone and a culture harvesting zone, the temperature regulation system, the flow-regulating system being within the culture chamber portion, the lighting system being within the culture concentrating zone and the biomass-directing flow propulsion device system causing a vertical flow of culture medium contained in the housing such that the biomass is concentrated in the culture concentrating zone.

Advantageously, the biomass-directing flow propulsion device allows to concentrate the biomass within the culture chamber portion into a culture concentrating zone independently of, or against, the gravity effect within the photobioreactor that tends to induce, during the culturing process, the biomass to slowly settle at the bottom of the culture chamber portion from the photobioreactor.

The biomass-directing flow propulsion device may be configured to advantageously create two opposite vertical flows of the biomass medium to transport and concentrate the biomass into the culture concentrating zone located essentially in an intermediate or central portion of the culture chamber portion, while allowing homogeneous mixing of the concentrated biomass.

The flow regulating system allows to increase the residence time of the biomass (e.g. thereby concentrating and maintaining the biomass) within a defined zone from the culture chamber portion called culture concentrating zone wherein culture parameters (e.g. temperature, nutrient concentration, pH, nutrient gas concentration, lighting) are adjusted to obtain optimal growing rates and conversion yields (e.g. growing yields, production yields of biomass derived products), while providing homogeneous mixing of the concentrated biomass within this culture concentrating zone to avoid culture limiting factors to occur such as local overheating, local excessive light radiation, insufficient light radiation, local pH variations, and to increase the surface contact between nutrient gas and the concentrated biomass. Further, the flow regulating system allows a gentle and low shear mixing of the concentrated biomass within this culture concentrating zone avoiding any traumatic damage to the biomass, while inducing the homogeneous dispersion of metabolic gases (e.g. $O_2$ and $H_2$) expelled at the surface of the culture medium to facilitate their collection. Typically, the cell population density within the culture concentrating zone ranges from about 1 to about $50 \times 10^{10}$ cells per milliliter in the case of *Chlorella vulgaris*.

Advantageously, the temperature regulation system allows controlling the temperature within the culture chamber portion and in particular within the culture concentrating zone in order to adjust the temperature to an optimal value to obtain optimal growing rates and/or conversion yields.

A photobioreactor according to the invention may further comprise a gas feeding system, a feeding device and a harvesting system.

A photobioreactor according to the invention may further comprise a feed-back control unit.

Advantageously, the feed-back control unit allows to both constantly monitor and rapidly adjust culture parameters to obtain optimal growing rates and conversion yields. Further, the feed-back control system allows the rapid detection of operating dysfunctions or culture contamination. In particular, the feed-back control unit allows operating the photobioreactor according to the invention in a continuous or semi-continuous mode.

A photobioreactor according to the invention may comprise a lighting system comprising a light source holder device, a light controlling unit and a rotating support having a drive. Advantageously, such lighting system allows homogeneous lighting (e.g. lighting time, intensity) of the biomass concentrated within the culture concentration zone, while providing further homogeneous mixing.

Advantageously, a photobioreactor to the invention may comprise a light source holder device comprising at least one light source holder and a plurality of light sources mounted on the light source holder such that the light sources are arranged essentially parallel to the axis of the photobioreactor and are substantially evenly distributed within the culture concentrating zone.

A photobioreactor according to the invention may comprise a gas feeding system comprising a gas bubble distribution platform comprising a gas gate and a gas pressure regulation device. The gas gate may comprise gas passages and a gas flow regulator.

A photobioreactor according to the invention may comprise a culture mixing and concentrating entity comprising a biomass-directing flow propulsion device comprising blades mounted on a rotating support having a drive. Advantageously, the blades should be profiled and the rotating speed of the rotating support of those blades should be adjusted to direct the biomass towards the concentrating culture zone, to maintain the so concentrated biomass within this culture concentrating zone and to provide a non-traumatic mixing of the biomass. Typically, the rotating speed of the rotating support of those blades from the biomass-directing flow propulsion device ranges from about 0.1 to above 60 rpms depending upon the diameter of the reactor and of the susceptibility of the type of organism cultivated to shear stress.

A photobioreactor according to the invention may comprise a feed-back control unit comprising a sample collection unit, a sample analyzer and a control device. The sample analyzer may further comprise at least one sensor to analyze the culture sample and a computer acquisition system. Advantageously, the feed-back control unit further allows the continuous or semi-continuous measure of parameters indicative of the size and/or density of the biomass cells present in the culture sample and the instant adjustment of culture parameters to obtain optimal growing rates and conversion yields based on the value of the measured parameters.

Advantageously, the housing of the photobioreactor allows to work under a pressure higher than the atmospheric pressure, thereby inducing an increase in the concentration of the nutrient gas within the culture medium. Typically, the housing of the photobioreactor is suitable to work under absolute pressures from 1 mbars up to and above 5 bars.

Further disclosed herein is a production plant comprising at least one photobioreactor according to the invention.

Further disclosed herein is a method for growing photosynthesizing biomass on a continuous or semi continuous mode comprising:
(i) providing a photosynthesizing culture in an aqueous culture medium into a temperature-regulated culture chamber portion;
(ii) feeding the photosynthesizing culture with nutrients;
(iii) mixing and concentrating the said photosynthesizing culture into a culture concentrating zone from the said culture chamber portion;
(iv) homogeneously providing nutrient gas to the photosynthesizing culture medium;
(v) homogeneously providing a controlled light exposure to the said photosynthesizing culture in the concentrating zone from inside the culture medium;
(vi) continuously or semi-continuously harvesting a biomass from the said photosynthesizing culture.

Further objects and advantageous aspects of the invention will be apparent from the claims and from the following detailed description of embodiments of the invention with reference to the annexed drawings in which:

BRIEF DESCRIPTION OF THE DRAWINGS

FIG. 5A illustrates photobioreactors $R^1$ and $R^2$ in series for culturing microorganisms at different development stages and FIG. 5B illustrates a photobioreactor $R^1$ for culturing microorganisms arranged in series with bioreactors for bioconversion ($R^2$ and $R^3$ arranged in parallel).

DETAILED DESCRIPTION

Figure 1:
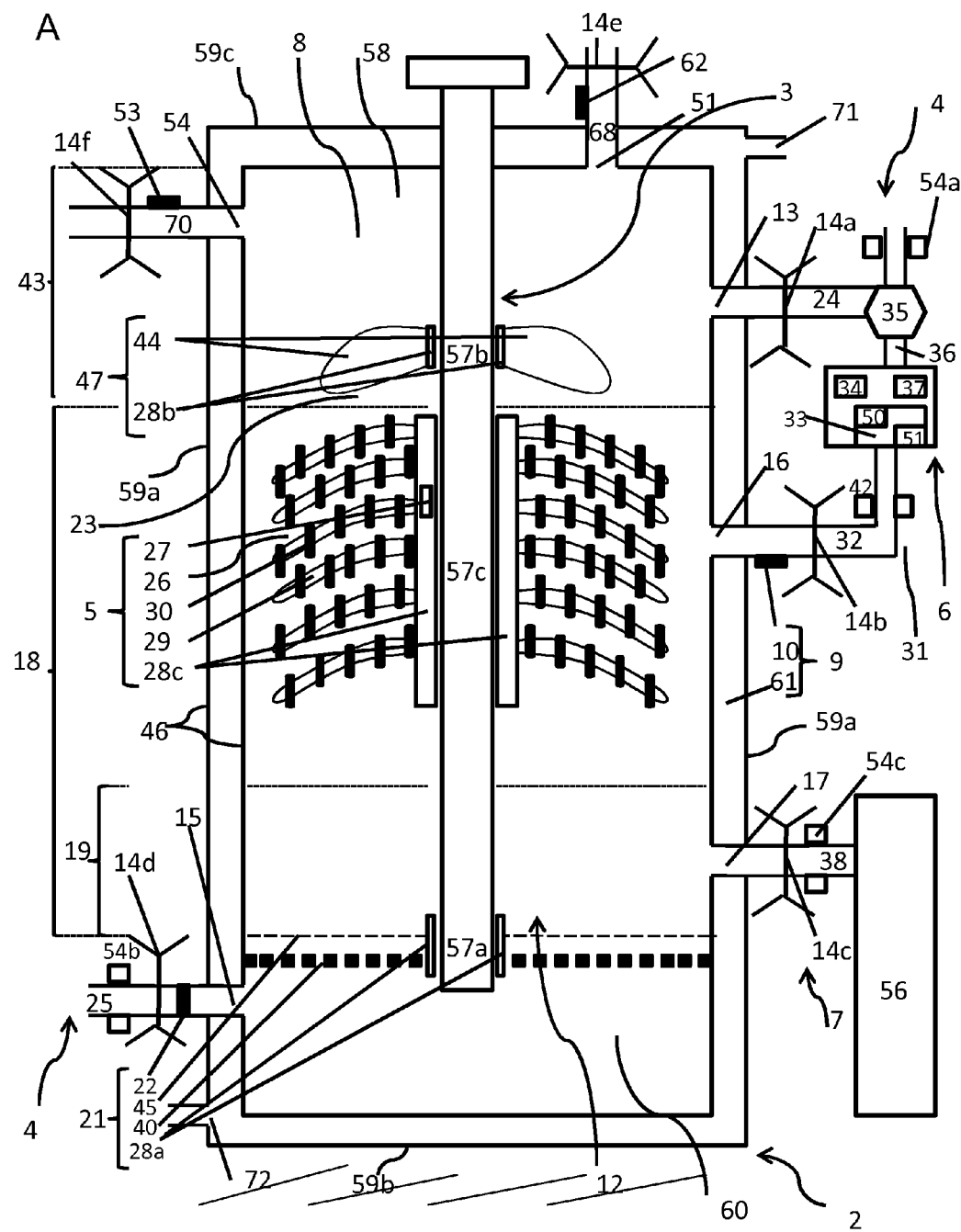
FIG. 1A is a cross-sectional view of a photobioreactor according to an embodiment of the invention.
FIG. 1B is a cross-sectional view of a photobioreactor according to another embodiment of the invention.
Figure 1:
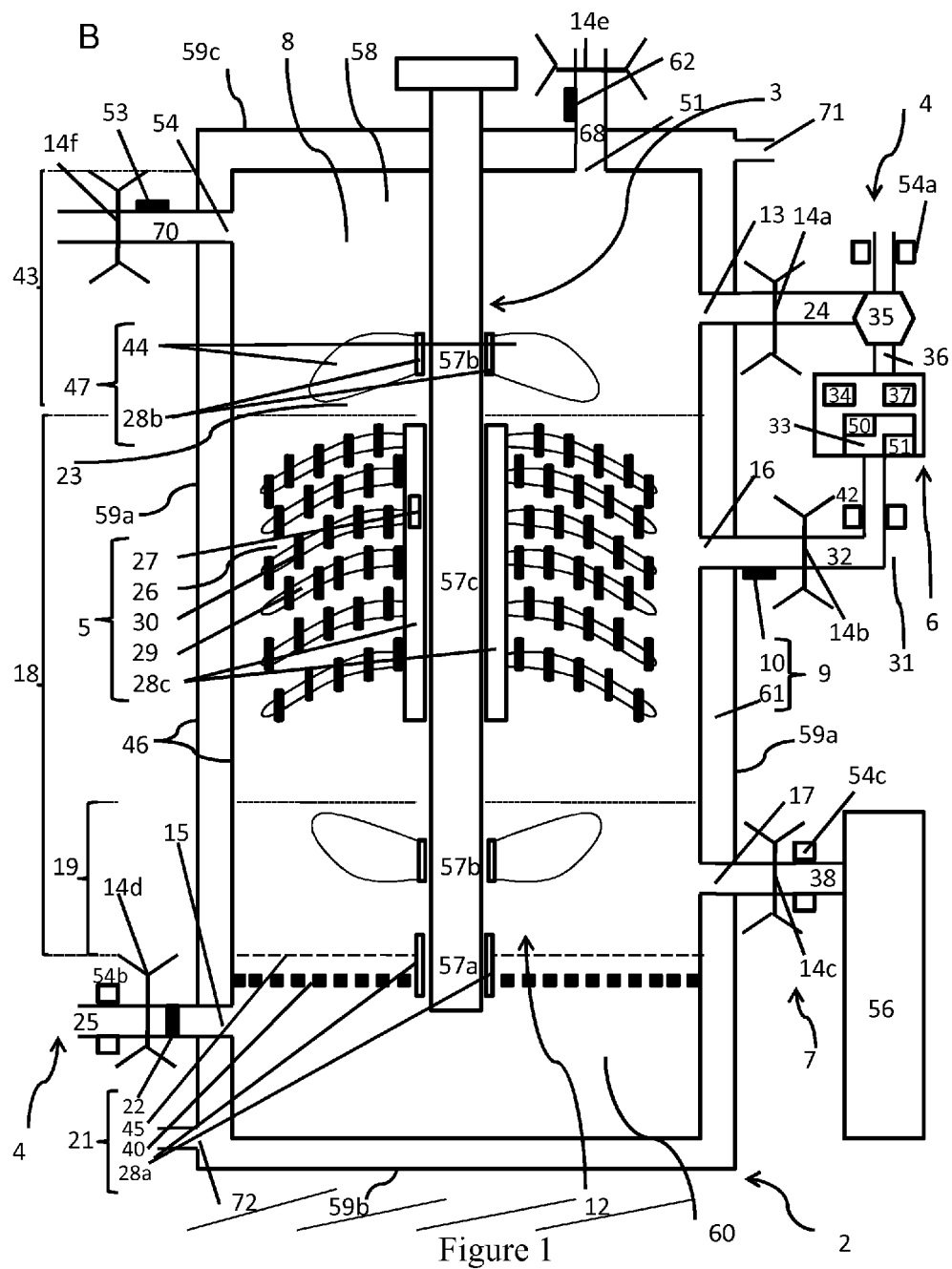

Referring to FIG. 1, a photobioreactor 1 according to an embodiment of the invention comprises a housing 2 defining an interior chamber 58 comprising a culture chamber portion 8 for containing a liquid culture medium and a gas feeding chamber portion 60, a temperature regulation system 9, a flow-regulating system 3 comprising a culture mixing and concentrating entity 23 comprising a biomass-directing flow propulsion device 47 and a lighting system 5. The culture chamber portion 8 comprises a culture concentrating zone 18, a culture harvesting zone 19 and a gas collecting zone 43, the temperature regulation system 9, the flow-regulating system 3 being arranged within the culture chamber portion 8 and the lighting system 5 being arranged within the culture concentrating zone 18. The photobioreactor 1 according to an embodiment of the invention further comprises a gas feeding system 12, a feeding device 4 and a harvesting system 7.

The interior chamber 58 is enclosed by bioreactor housing 59 comprising side, floor and top walls 59a, 59b, 59c connected to at least one upper feeding port 13 closable by a valve 14a, at least one lower feeding port 15 closable by a valve 14d in fluid communication with the gas feeding chamber portion 60 and at least one outflow port 17 at the level of the culture harvesting zone 19 and closable by a valve 14c.

The temperature regulation system 9 is configured for controlling the temperature of the culture medium within the culture zone 8 and in particular within the culture concentrating zone 18 and comprises a temperature sensing element 10 and a heating/cooling member 61.

The gas feeding system 12 comprises a gas bubble distribution platform 21 configured for delivering and controlling the delivery of gas bubbles, in particular nutrient gas bubbles, to the culture medium within the culture chamber portion 8, in particular in the culture concentrating zone 18. The gas bubble distribution platform 21 comprises a gas gate 40 and a gas pressure regulation device 22. The gas gate 40 is configured to control the size, the flow and the trajectories of the gas bubbles entering the culture chamber portion 8 from the gas feeding chamber portion 60. The gate 40 comprises gas passages 41 (FIG. 4) for conducting the gas from the gas feeding chamber portion 60 into the culture chamber portion 8 and a gas flow regulator 45 for regulating the gas flow through those passages 41. The gas flow regulator 45 comprises a rotating support 28a having a drive 57a whose rotation axis is essentially parallel to the axis of the photobioreactor. The gas pressure regulation device 22 is configured to control the gas pressure inside the gas feeding chamber portion 60 and comprises at least one pressure sensor.

The gas feeding chamber portion 60 may be partially filled with liquid and solid mixing elements such as glass balls whose function is to break the gas stream entering the gas distribution platform 21 into bubbles of small diameter.

Venturi mixers enable to reach sizes as small as 40 μm and can be installed on the gas feed line 25 directly feeding the bubbles in the liquid contained in the gas feeding chamber 60.

The flow-regulating system 3 is configured to concentrate the photosynthesizing biomass in suspension in the culture medium into a zone of the culture chamber portion 8 called culture concentrating zone 18. The flow-regulating system 3 comprises a culture mixing and concentrating entity 23 comprising a biomass-directing flow propulsion device 47 comprising blades 44 mounted on a rotating support 28b having a drive 57b whose rotation axis is essentially parallel to the axis of the photobioreactor.

The lighting system 5 is configured to provide the photosynthesizing biomass in suspension in the culture medium with a controlled lighting in terms of intensity, wavelength, lighting time and lighting cycles (on and off) of the light sources 30 in a homogeneous manner in the concentration zone 18 (for example each element of volume within the concentration zone 18 may receive essentially the same illumination duration and intensity). The lighting system 5 comprises a light source holder device 26, a light controlling unit 27 and a rotating support 28c having a drive 57c whose rotation axis is essentially parallel to the axis of the photobioreactor. The light source holder device 26 comprises at least one light source holder 29 and a plurality of light sources 30 mounted on the light source holder 29 such that the light sources 30 are arranged essentially parallel to the axis of the photobioreactor and are distributed essentially evenly within the culture concentrating zone 18. The light controlling unit 27 is configured to monitor independently the intensity, the wavelengths, the lighting time and the lighting cycles (on and off) of the light sources 30.

The feeding device 4 comprises an upper feeding line 24 in fluid communication with the upper feeding port 13 through the aperture of a valve 14a and a lower feed line 25 in fluid communication with the lower feeding port 15 through the aperture of a valve 14d. The upper feeding line 24 is configured to introduce culture feeding material such as culture medium (e.g. water) and nutrients (e.g. nitrogen such as in the form of nitrates, salts and minerals) and the photosynthesizing biomass into the culture zone 8. The lower feeding line 25 is configured to introduce gas into the gas feeding chamber portion 60. The harvesting system 7 is configured to harvest the cultured biomass on continuous or semi-continuous mode from the photobioreactor and comprises an outflow line 38 in fluid communication with a harvesting reservoir 56 through an outflow valve 14c.

The photobioreactor may further comprise a feed-back control unit 6 configured to independently control various parameters of the culture medium such as temperature, lighting, pH, gas flow, gas pressure, nutrient concentration, size and density of the culture concentration zone 18 through the instant analysis of a culture sample within the culture concentration zone 18 and a feed-back action on those parameters depending on the results of the sample analysis. In particular, the feed-back control unit 6 is configured to control the residence time of the photosynthesizing biomass within the concentration zone 18. The feed-back control unit 6 comprises a sample collection unit 31, a sample analyser 33 and a control device 37.

The sample collection unit 31 is configured to collect a culture sample from the culture concentrating zone 18 through a control port 16 in a wall 59a from the housing 2 in a continuous or semi-continuous mode. The sample collection unit 31 comprises a control line 32 put in fluid communication with a control port 16 through the aperture of a valve 14b and a pump 42. The pump 42 is configured for collecting a sample from the culture medium within the concentration zone through the control line 32 and for driving the collected sample to the sample analyzer 33.

The sample analyser 33 comprises at least one sensor 50 to analyse the culture sample and a computer data acquisition system 51 for storing data from the analysis and comparing them to standard values previously stored in the computer data acquisition system 51. The computer data acquisition system 51 is configured to send information to the control device 37 on any deviation from standard values regarding the culture condition parameters such as temperature, gas pressure, cell density and size, pH, $CO_2$ concentration in the concentration zone 18 from the culture chamber portion 8.

The control device 37 is configured to control independently the operation of the temperature regulation system 9, the gas feeding system 12, the flow-regulating system 3, the lighting system 5, the harvesting system 7 and the feeding device 4 based on the information received from the computer data acquisition system 51 regarding the culture condition parameters. The control device comprises a multiple valve actuator 34 configured to monitor the flow into the upper feeding line 24, the lower feeding line 25, the control line 32 and the outflow line 38 though the command of the upper feeding valve 14a, lower feeding valve 14d, control valve 14b and outflow valve 14c, respectively.

The feed-back control unit 6 may further comprise a sample reinjection line 36 in fluid communication with the upper feeding line 24 through the opening of a multiport valve 35 for re-injecting the sample (e.g. water, dissolved nutrients, biomass, dissolved gases) collected in the sample collection unit 31 into the culture chamber portion 8. The multiport valve 35 is configured to be also actuated by the multiple valve actuator 34.

The walls 59a or 59c in the upper part of the housing 2, in the gas collecting zone 43 above the surface of the liquid medium in the culture chamber portion 8, may further comprise a venting outlet 51 in fluid communication with the exterior of the photobioreactor through the aperture of a valve 14e. The venting outlet 51 is configured to collect gas from the photobioreactor e.g. unused $CO_2$ or produced $O_2$ or $H_2$. The valve 14e is configured to be also actuated by the multiple valve actuator 34. The venting outlet 51 may be connected to a gas collector system through a venting gas line 68, the gas collector system 67 being configured to capture and eventually to purify the gas collected from the venting outlet 51.

The walls 59a or 59c in the upper part of the housing 2, in the gas collecting zone 43 above the surface of the liquid medium in the culture chamber portion 8 may further comprise an overflow sensor 53, an overflow outlet 54 in fluid communication with the exterior of the bioreactor through the aperture of a valve 14f. The overflow sensor 53 is configured to send information regarding the level of the surface of the liquid medium in the culture chamber portion 8 to the computer data acquisition system 51 from the feed-back control unit 6 and/or to control an alarm in the control device 37 in the case of malfunction resulting in an increase of the liquid level in the culture chamber portion 8 above a predetermined level. The valve 14f is configured to be also actuated by the multiple valve actuator 34. The overflow outlet 54 may be connected to an overflow collector system through an overflow line 70, the overflow collector system 69 being configured to capture the liquid culture overflow collected from the overflow outlet 54. The captured liquid culture may then be sent to the waste management section of an industrial plant.

The photobioreactor may further comprise pumps 54a and 54b configured to pump the nutrients and gas from the nutrient and gas sources into the upper and lower feeding lines 24 and 25, respectively. The photobioreactor may further comprise a pump 54c configured to pump the harvested culture from outflow line 38. Pumps 54a, 54b, 42, 54c are any suitable device capable of pumping the suspension without harming the cells. In a particular embodiment, suitable pumping systems are those which do not create shear stress at the level of the cell membrane such as reciprocating or peristaltic pumps. Examples of other suitable devices include, without limitation, centrifugal pumps, impeller pumps, or rotary pumps.

In a particular advantageous embodiment, the photobioreactor according to the invention is suitable to work under pressure and comprises an air-tight pressure resistant housing 2.

Suitable materials which can be used to form the housing 2 of the photobioreactor include but are not limited to stainless steel or any polymer or copolymer having ultraviolet resistance properties such as polycarbonates, acrylic resins, polypropylene, polyethylene, polyvinylchloride and glass, and/or the same coated with specific coatings exhibiting light filtering. Typically, the interior walls 59a, 59c and eventually 59b of housing of the photobioreactor may be made of or coated with a biocompatible material selected from the above list or can be coated with coatings exhibiting lipophobic properties in order to avoid agglomeration of matters, such as surface coatings comprised of at least two layers depending on the substrate and the environment the reactor will be placed in. In general, the layers that contact the reactor surface are typically metal oxides, nitrides, oxynitrides, borides or carbides. The interlayer may also be comprised of CMOS (complementary metal-oxide semiconductor materials). Interlayers are used for adhesion as well as metallurgic properties. The functional layer which faces the liquid mixture in the culture chamber portion 8 may be saturated with fluorine moieties, and this surface may be modified to interact with specific chemicals, protein sites in prescribed manners.

The heating/cooling member 61 may advantageously be in a form of a thermal fluid (e.g. a liquid or a gas) circulating within an internal envelope 46 (e.g. double jacket walls) presenting a thermal fluid inlet 71 and a thermal fluid outlet 72 inside the walls 59 from the housing 2, the heating/cooling member 61 being configured to heat/cool the thermal fluid under the control of the temperature sensing element 10.

Figure 4:
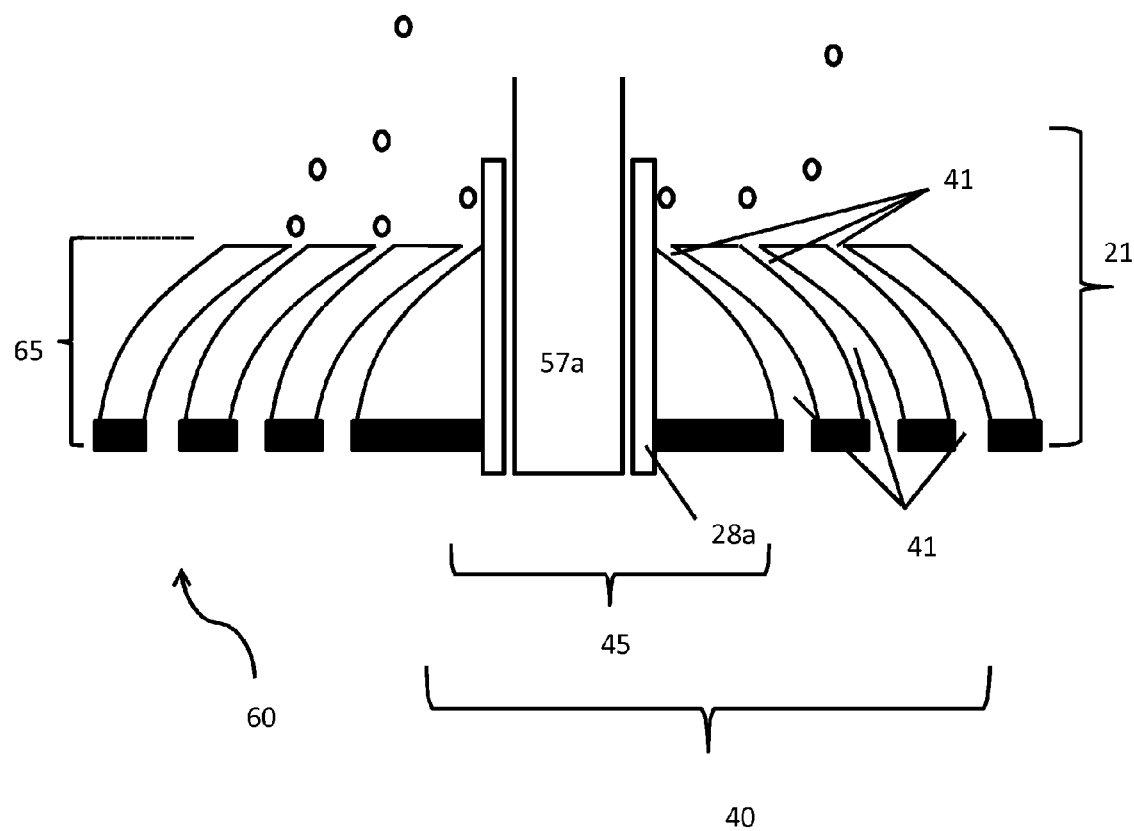
FIG. 4 schematically depicts a cross-sectional view of a gas bubble distribution platform according to an embodiment of the invention wherein a gas gate is achieved by profiled gas passages made in a perforated plate so that gas bubbles are released in the culture chamber portion non-vertically to the gas bubble distribution platform surface.

The gas passages 41 may be formed of nozzle heads, perforations in a plate, or a grating or wire mesh. The gas passages 41 in the form of perforations in a plate may be in a form of straight holes or profiled channels that are configured to liberate gas bubbles at oblique angle to the vertical (axial) direction, up to tangentially or almost tangentially to the surface of the gas gate 40 as shown in FIG. 4. This advantageously assists in increasing the residence time of the gas bubbles within the culture concentration zone 18. In particular, the gas bubble distribution platform 21 presents the advantage of maximizing carbon dioxide absorption rate by introducing $CO_2$ in the culture concentrating zone 18 in the form of bubbles of small size having a vertical speed as low as possible and dispersing those homogeneously within the culture concentrating zone 18. Typically, $CO_2$ bubbles having an average diameter from about 40 μm to about 5 mm can flow through the gas distribution platform 21.

In a particular embodiment, the gas gate 40 is located essentially at the bottom of the culture concentrating zone 18. The lower feeding line 25 may be in fluid connection with a $CO_2$ storage tank The $CO_2$ fed into the gas feeding chamber portion 60 may be $CO_2$ extracted from the atmosphere or $CO_2$ generated from a biomass digester or $CO_2$ generated from an electrical power plant burning carbon-based fuel (e.g. coal, oil, natural gas, or cellulosic materials) or any combination of the foregoing. The $CO_2$ rich-effluent-gas stream passes first through a gas cleaning unit where poisons such as oxides (e.g. phosphorus oxides, Pox; nitrogen oxides, Nox) and heavy metals known as having an antibiotic property such as salts of silver are removed and/or transformed into useful ingredients such as nutrients before entering the gas chamber 60 from the photobioreactor. Technologies available for capturing $CO_2$ and for cleaning $CO_2$ feed are well known in the art.

The flow regulator 45 may be formed by gas passages 41 mounted on the rotating support 28a or by a perforated plate or a grating or wire mesh mounted essentially perpendicular to the rotation axis of the rotating support 28a over the gas passages 41. The perforated plate or grating or mesh advantageously present holes or channels distributed essentially evenly on their entire surface and disposed at the interface between the gas feeding chamber portion 60 and the culture chamber portion 8, in particular in the proximity of the culture concentrating zone 18.

In a particular embodiment, the light source holders 29 are made of or coated with a biocompatible polymer material which prevents the deposit of culture material on its surface such as described above. In a particular embodiment, suitable materials which can be used to form the light source holders 29 or the housing of the light sources include but are not limited to any polymer and/or copolymer which is clear, excellent in light transmission and has ultraviolet resistance properties such as polycarbonates, acrylic resins, polypropylene, polyethylene, polyvinylchloride and glass, and/or the same coated with specific coatings exhibiting light filtering and concentration properties.

Figure 3:
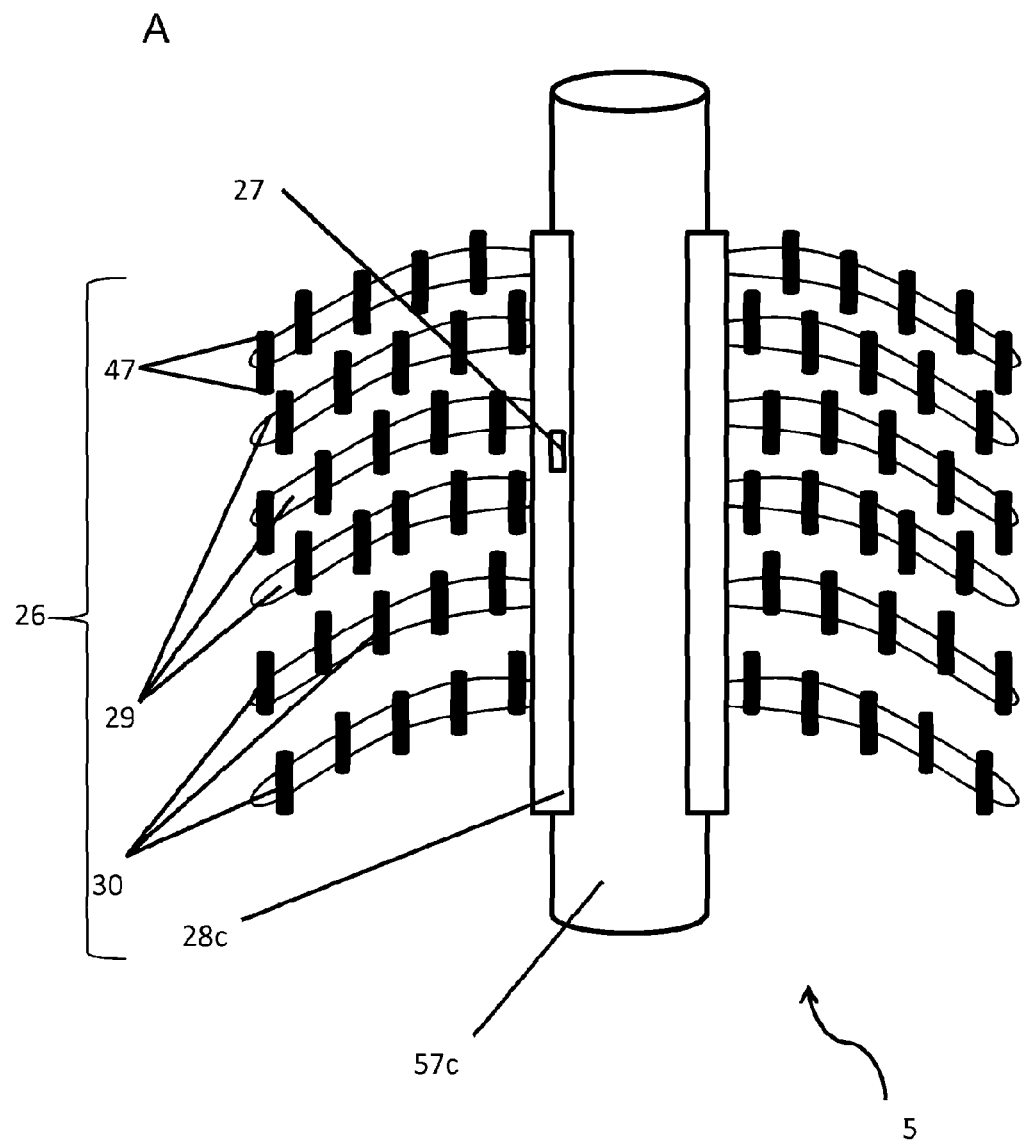
FIG. 3A is a schematic cross-sectional view of a lighting system of the photobioreactor according to an embodiment, illustrating a light source holder device and rotating support viewed parallel to the photobioreactor axis.
FIG. 3B is a schematic cross-sectional view of a light source holder device and rotating support viewed perpendicular to the photobioreactor axis according to an embodiment of the invention.
FIG. 3C is a schematic view of an arrangement of light sources seen in a plane perpendicular to the photobioreactor axis according to an embodiment of the invention.
Figure 3:
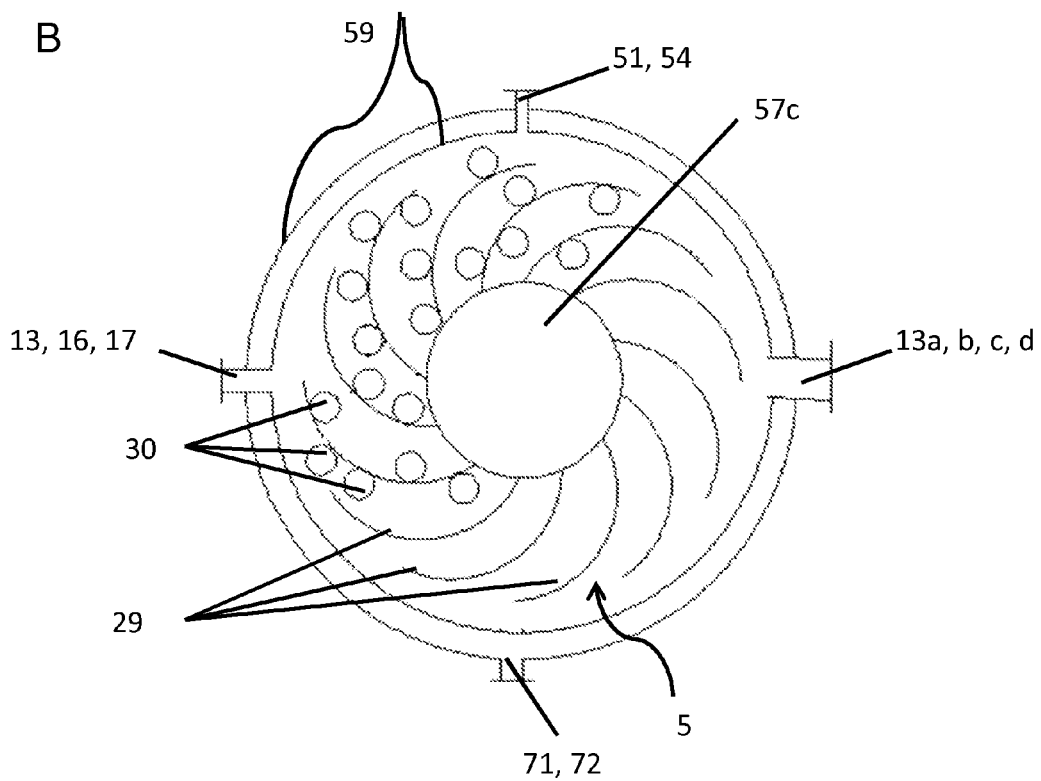
Figure 3:
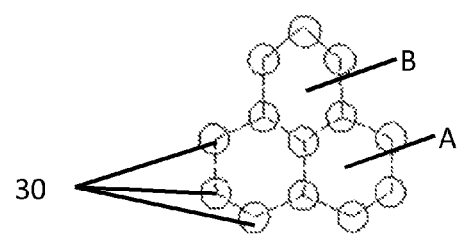

In other particular embodiments, the light source 30 may comprise an arrangement of submersible light emitting diodes (LEDs), luminescent tubes or optical fibers. The LEDs, luminescent tubes or optical fibers may be mounted essentially parallel to the axis of said photobioreactor on a light source holder device 26 like shown on FIGS. 3A & B. For example, the light source 30 may comprise a combination one or more LEDs or luminescent tubes or optical fibers for emitting light with a wavelength in the range of about 380 nm to about 800 nm. The light controlling unit 27 may monitor lighting cycles of light sources 30 which typically comprise switching the light sources on and off in a cycle of about 1 to about 10 seconds on and about 1 to about 10 seconds off, typically about 1 second on and about 6 seconds off.

Adjacent light sources 30 may be spaced within the culture concentrating zone 18 at a distance which is less than or equal to the distance beyond which the photosynthesizing energy of the light source is insufficient to generate effective photosynthesis (also called $D_{max}$). In a further particular embodiment, the light sources are spaced within a plane perpendicular to the axis of the photobioreactor such that each element of volume within the concentration zone 18 receives essentially the same illumination duration and intensity independently from its distance from the axis of rotation of the lighting system 5, i.e. the distance between two adjacent light sources within a plane perpendicular to the axis of the photobioreactor are adjusted to the distance separating this light source to the axis of rotation of the lighting system 5. For example, if $D_1$ corresponds to the $D_{max}$ value for a light source located at a distance $r^1$ from the axis of rotation of the lighting system 5, the $D'_{max}$ value for a light source located at a distance $r_2$ from the axis of rotation of the lighting system 5 ($D_2$) will be adjusted as follows: $D_2=D_1*r_2/r_1$. A schematic representation of such an arrangement is drawn on FIG. 3C where an element A or B from the culture concentrating zone 18 will receive essentially the same illumination duration and intensity from the light sources 30.

In another embodiment, the lighting time of the light sources within a plane perpendicular to the axis of the photobioreactor is regulated by the light controlling unit 27 such that each element of volume within the concentration zone 18 receives essentially the same illumination duration and intensity independently from its distance from the axis of rotation of the lighting system 5, i.e. the illumination times of light sources within a plane perpendicular to the axis of the photobioreactor are adjusted to the distance separating a light source to the axis of rotation of the lighting system 5. For example, if $T_1$ corresponds to the illumination time value for a light source located at a distance $r_1$ from the axis of rotation of the lighting system 5, the illumination time value for a light source located at a distance $r_2$ from the axis of rotation of the lighting system ($T_2$) will be adjusted as follows: $T_2 = T_1 * r_2/r_1$.

In a particular embodiment, the light sources 30 may be spaced within the culture concentrating zone 18 at distances in the range of about 1 to about 15 cm along the axis of the photobioreactor, and distances in the range of about 1 to about 15 cm perpendicularly to the axis of the photobioreactor.

Figure 2:
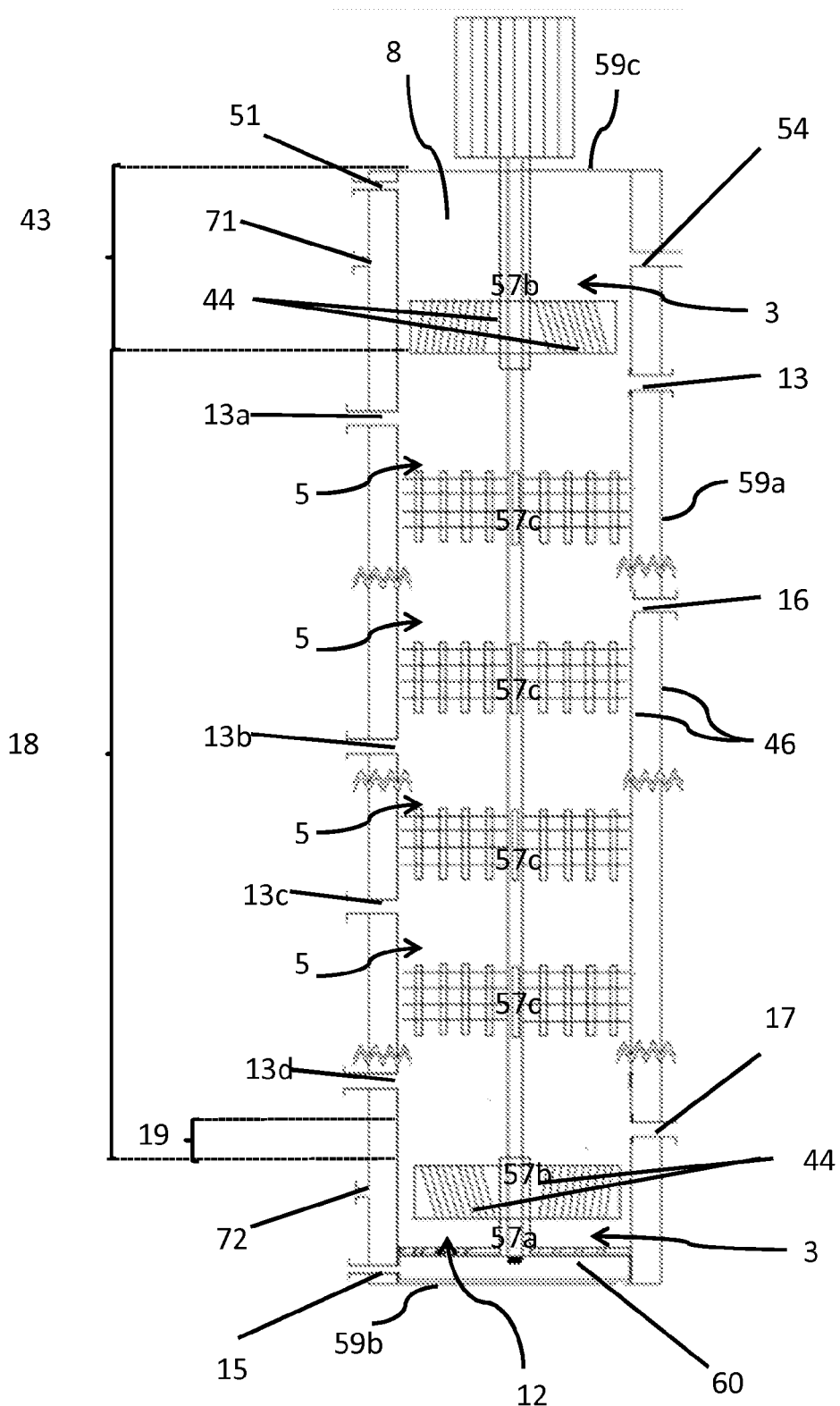
FIG. 2 is a cross-sectional view of a photobioreactor according to another embodiment of the invention, the photobioreactor comprising a culture mixing and concentrating entity having a plurality of ensembles of blades mounted on a rotating support, a plurality of ensembles of light source holder devices mounted on a rotating support and a plurality of feeding lines.

In a particular embodiment, the lighting system 5 may be formed of a plurality of light source holder devices 26 essentially parallel to each other within the culture concentration zone 18 for example as shown on FIG. 2C.

In a particular embodiment, the wavelengths of the light emitted by the light sources 30 may vary depending upon their distance from the central axis within a plane perpendicular to the axis of the photobioreactor.

In a particular embodiment, Chorella pyrenoidosa is grown using artificial lighting of about 458 nm (blue region of the spectrum, strong chlorophyll absorption and morphogenic effect) and about 633 nm (red region of the spectrum strong chlorophyll absorption, morphogenic and ontogenetic effects).

In a particular embodiment, wavelength between about 380 and about 510 nm are used for culturing cells in the exponential phase of their growth cycles. In another particular embodiment, wavelengths between about 620 and about 710 nm are used for culturing cells in the beginning of their growth cycles.

The light controlling unit 27 comprises an electrical circuit configured to control the operation of the light sources 30 (e.g. time & frequency of the lighting cycles, light intensity, light wavelength), typically through an external computer system that can be electronically connected to the control unit 37 from the feedback control unit 6.

In a particular embodiment, the flow-regulating system 3 comprises one culture mixing and concentrating entity 23 and the concentrating zone 18 is essentially located at the bottom of the photobioreactor (FIG. 1). In another particular embodiment, the flow-regulating system 3 is formed of a plurality of culture mixing and concentrating entities 23. In a further particular embodiment, the flow-regulating system 3 comprises two culture mixing and concentrating entities 23 rotating around the same axis essentially parallel to the photobioreactor axis but in opposite directions (e.g. clockwise and counter clock wise in a plane essentially perpendicular to the photobioreactor axis) and the concentrating zone 18 is located essentially in the middle of the photobioreactor for example as shown on FIGS. 2A and B.

The rotating supports 28a, 28b and 28c may be driven independently by separate drives 57a, 57b and 57c or alternatively driven together by the same drive. In a particular embodiment, the rotation speed of the drives 57a, 57b and 57c are independently retro-controlled by the control device 37 from the feed-back control unit 6.

The culture feed-back control unit 6 may be advantageously formed by a sample collection unit 31 configured for the collection of culture samples from the culture concentrating zone 18 at predetermined time intervals, for instance between 1 second to 10 minutes through the control line 32.

The sample analyser 33 may comprise at least one sensor 50 for measuring culture sample parameters such as pH, temperature, dissolved carbon dioxide concentration, oxygen concentration, gas pressure and partial pressures, nutrient concentration (e.g. nitrates), size and density of cultured cells common on photobioreactors. For example, cell size and/or number may be assessed by the sample analyser 33 through the measurement of cell number/size in a culture sample by flow cytometry such as described in Arino J., *Modélisation structurée de la croissance du phytoplancton en chemostat; Université J Fourrier, Thesis Jan.* 12, 2001 and thereby instantly determine in which phase (e.g. latence, exponential growth, decay) of cell life cycle is predominantly the sample analysed, notably advantageously in the case of unicellular algae having short doubling times. For example, cell density may be assessed by a sample analyser 33 through the measurement of turbidity of a culture sample by absorption spectrophotometry (e.g. 680 and 800 nm).

Depending on the value of the parameters measured by the sample analyzer 33 as compared to reference values for those parameters (e.g. previously stored in the computer data acquisition system 51), the multiport valve actuator 34 from the culture feed-back control unit 6 is configured to command independently the aperture of valves 14a and 14d from the feeding lines 24 and 25 for feeding the culture with nutrients and gas, the aperture of valve 35 for re-injecting the culture sample into the feeding line 24, the aperture of valve 14c for harvesting the culture into an outflow line 38 and the aperture of valve 14e for venting gas, the aperture of valve 14f for collecting the liquid overflow into an overflow line 70.

In a particular embodiment, the feeding device 4 may further comprise further feeding lines 24a in fluid communication with further feeding ports (e.g. 13a, 13b, 13c, 13d) through the aperture of a corresponding valve (FIG. 2B). Those further feeding lines 24a are configured to further introduce culture feeding material such as culture medium (e.g. water) and nutrients (e.g. nitrogen such as in the form of nitrates, salts and minerals) and the photosynthesizing biomass into the culture zone 8. The corresponding valves are configured to be actuated by the multiport valve actuator 34 from the feed-back control unit 6.

Any suitable photosynthesizing microorganism may be cultured in the photobioreactor of the invention. For example, a photobioreactor according to the invention is suitable to grow aqueous microorganisms, in particular a photosynthesizing bio-culture, in particular microalgae (e.g. Viridaeplantae (Chlorella, Chlorophycophyta), Chrysophycophyta (golden algae), Rodophyta (red algae), stramenopiles (diatoms and algae, from the Bacillariophyceae family, phaecophytophyta brown algae), photosynthetic prokaryotes such as cynobacteria, photosynthesizing eukaryotes excluding charales family, Spirulina, Nanochloropsis, Prorocentrum Minimum), at a large scale in a continuous, semi continuous (e.g. pulsed) flow or batch mode.

A photobioreactor according to the invention is also suitable to grow the most common algae species used in aquacultures such as for example *Isochrysis affinis galbana, Chatetoceros gracillis, Chaetoceros calcitrans, Tetraselmis suesica, Thalassiosira pseudonana, Pavlova lutheri, Isochrysis galbana, Nannochloropsys* and other species as: marine species like *Fragilaria sublinearis, Cylotella nana, Pavlova gyrens, Monochrysis lutheri, Prymnesium paruum* and *Nitzschia palea* and fresh water species: *Cyclotella* spp, *Scenedesmus* spp, *Navicula* spp, *Nitzschya* spp, *Chlamydomonas reinhardtii.*

Examples of further photosynthesizing microorganisms that can be advantageously grown in a photobioreactor according to the invention are vegetable tissues and monocellular organisms containing chloroplasts, photosynthesizing bacteria and algae such as those described in Gudin et al., 1986, *"Bioconversion of solar energy into organic chemicals by microalgae" in Advances in Biotechnological processes* 6, pp 73-110.

In a particular embodiment, a photobioreactor according to the invention is used for the production of photo-autotrophic cells, examples of which include *Chlorella, Scenedemus, Chlamydononas*, and *Cyanobacteria*.

In another embodiment, cells cultured in a photobioreactor according to the invention include those which have had their genome modified by genetic engineering techniques in order to produce specific metabolites, or to improve $CO_2$ fixation, or to improve other performance parameters.

In a particular embodiment, algae with short doubling time (e.g. 1 to 4 hours), high lipid content (e.g. >70%), resistance to shear stress are advantageous species for photosynthesizing biomass culture when biomass yield and biomass oil yield are considered as the operating objectives.

The choice of the photosynthesizing cell culture will depend on the operating objectives such as yield, nature of the metabolites and polysaccharides secreted and/or excreted from the microorganisms (Metting et al., 1986, *Enzyme Microbiol. Technol.*, 8, pp 386-394). Optimum values used for pH, temperature, nutrient, $CO_2$ and $O_2$ concentrations, lighting cycle, intensity and wavelengths will vary depending on the specific strain of microorganism, the nature of the metabolites and polysaccharides expected to be secreted and/or excreted from those microorganisms and the stage of the growth cycle of those microorganisms. These values can be determined by one of skill in the art.

According to one aspect, a photobioreactor according to the invention allows continuous or semi-continuous harvesting of a culture in addition to batch-harvesting carried out in known photobioreactor systems, thereby improving overall yield of the production plant (production yield and production rates). Further, a photobioreactor or a method according to the invention advantageously allows to control the residence time of the microorganism within the culture concentration zone 18 through the retro-control of the flow regulating system 3 by the feed-back control unit 6, the lighting efficiency within this zone by controlling the culture fluxes (feeding/concentrating/harvesting/recirculating) and the lighting cycles of the light sources 30 by the through the retro-control of the lighting system 5, the feeding system 4 and the harvesting system 7 by the feed-back control unit 6 and the residence time, concentration and flux of the nutrient gas (and thereby the pH) within the culture concentration zone 18 through the retro-control of the gas feeding system 12 by the feed-back control unit 6.

In a particular embodiment, the temperature regulation system is configured to regulate the temperature of the culture medium within the culture chamber portion 8 between about 16 and about 60° C., depending of the species to be grown, typically between about 29 and 32° C.

In a particular embodiment, the feed-back control unit 6 is configured to maintain the pH of the culture medium within the culture chamber portion 8 between about 7.5 and about 9.5 in fresh water, typically between about 6.0 and about 7.5 in salty water.

The photobioreactor according to the invention advantageously allows optimizing the lighting process by providing appropriate light exposure to the growing biomass at the right frequencies and intensity and for the right duration (only for the time required for the photosynthesis process to occur as photosynthesizing biomass cannot use light while it is absorbing and fixing carbon as part of its metabolic process), thereby avoiding photoinhibition and/or waste of incident photosynthesizing energy (light saturation).

Further, continuous or semi-continuous harvesting from a photobioreactor according to the invention enables maintaining a photobioreactor in optimal culture conditions for a specific phase of the life cycle of a microorganism and offers the possibility of optimizing production plants where those plants comprise more than one photobioreactor according to the invention.

Figure 5:
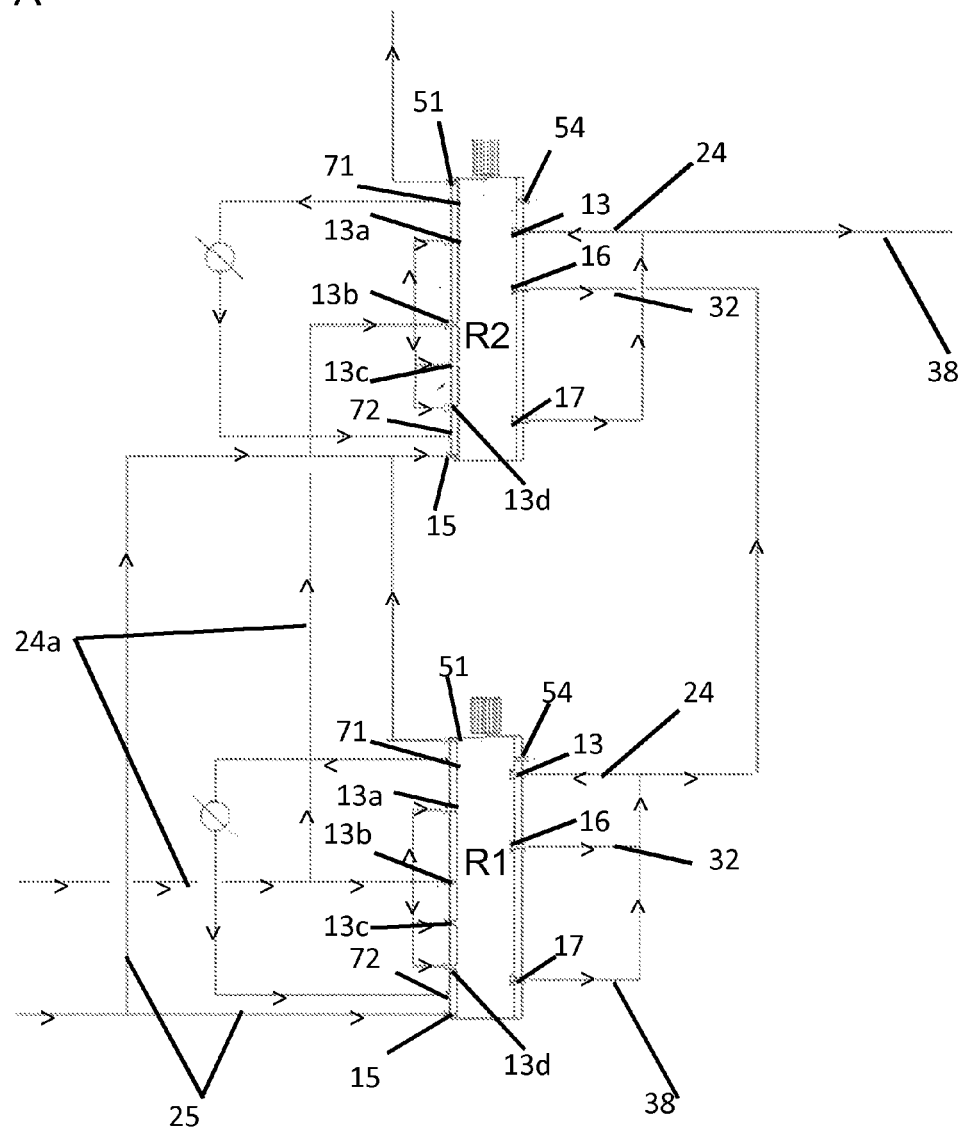
FIGS. 5A and 5B schematically illustrate photosynthesis culture systems according to embodiments of the invention showing a configuration of a plurality of photobioreactors arranged in series for culturing microorganisms, where
Figure 5:
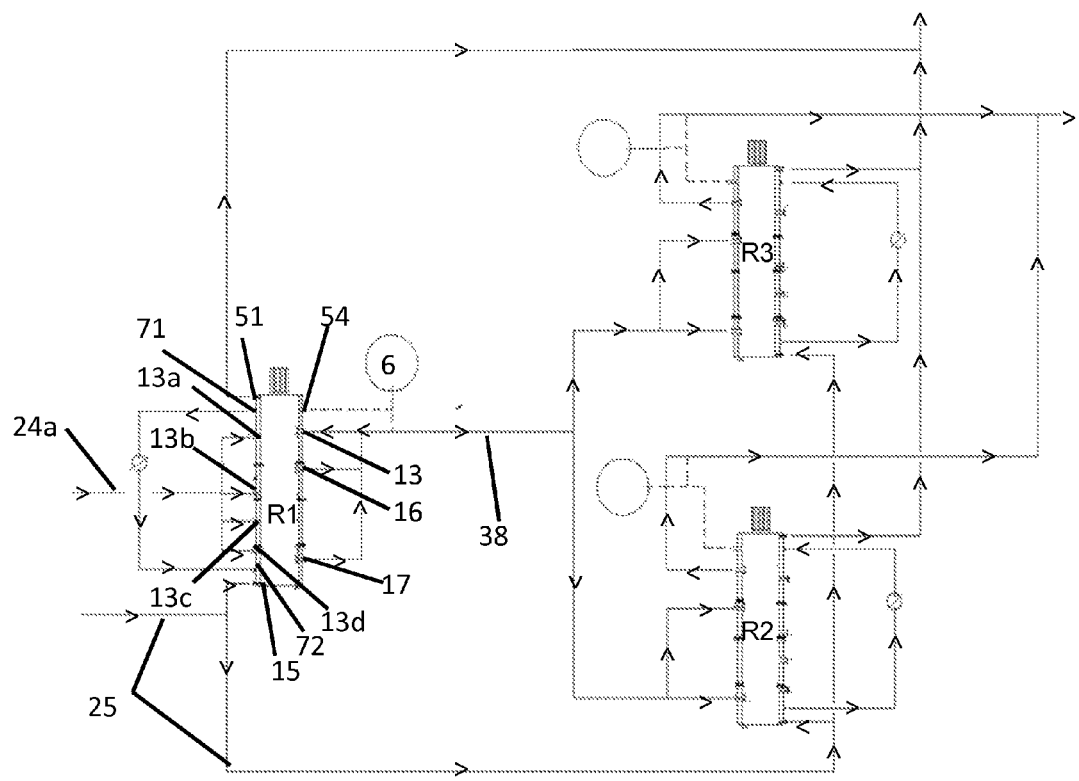

In an example, a plant may comprise more than one photobioreactor according to the invention for culturing microorganisms in series as shown on FIG. 5A. In this variant, each photobioreactor advantageously maintains the microorganisms in a specific and different phase of the life cycle (e.g. growth, division) in its culture concentrating zone 18 through the control of the corresponding specific culture conditions by a feed-back control unit 6. The microorganism culture is harvested through an outflowline 38 from a first photobioreactor $R^1$ at a specific development stage of a microorganism (e.g. division) and then fed into an upper feeding line 24 from a second photobioreactor $R^2$. Then, the microorganism culture is brought into a further development stage of a microorganism (e.g. growth, maturity) through the adjustment of the corresponding specific culture conditions by the feed-back control unit 6 of the second photobioreactor and then harvested through an oufflowline 38 from said second photobioreactor and then either fed into a further photobioreactor for reaching a further development stage or for bioconversion or for direct processing in case of raw algae or of food generated to feed shrimps for example.

In another example, a plant may comprise at least one photobioreactor according to the invention for growing microorganisms and at least one bioreactor for bioconverting those microorganisms (release of at least one substance selected from nucleic acids, proteins, carbohydrates (e.g. sugars) and lipids (e.g. oils or fatty acids) from the mature microorganisms), those bioreactors being arranged in series as shown on FIG. 5B. The culture harvested from an outflow line 38 from the growing photobioreactor $R^1$ is then sent downstream to processing sections of the plant. For example, the culture harvested from an outflow line 38 from the growing photobioreactor $R^1$ is fed into the feeding line 24a of at least one bioreactor $R^2$ for bioconversion (which can be a photobioreactor according to the invention or a conventional [bio]reactor). In case of a plurality of bioreactors for bioconversion may be arranged in parallel ($R^2$ and $R^3$).

Bioconversion results from submitting the culture medium to a certain stress, e.g. thermal stress by quenching the culture medium below a given temperature (typically, temperatures between about 4° C. and about 15° C. are used to provoke the bioconversion of unsaturated lipids contained in the cells), or energetic stress through modulation of the light intensity and/or wavelength and/or time of exposure, or both. These changes may be for example monitored by the control device 37.

The material resulting from bioconversion may be excreted from the cell or remain as intracellular product. In any case it has to be harvested and further processed to its final form as mentioned above.

The first step in downstream processing from the bioconversion reactor is to separate the organisms from their solvent (water in case of water solution). This is usually well performed by traditional centrifuges, either continuous or batch. Water is collected and recirculated via a tank in which the feeding solutions are prepared.

Releasing intracellular products necessitates breaking cell walls. The solution containing the stressed cells may then be fed to a state of the art apparatus such as a mechanical grinder, an ultrasonic grinder or any other appropriate existing technology. The products of interest may then be separated from the cell debris by exposing the "slurry" comprising those cell debris discharged from the grinders by state of the art separation technologies such as decantation, flocculation, filtration, depending on the respective physico-chemical properties of the components that have to be separated.

In some cases the biomass is just separated from the water, dried and then pelletized as energy containing pellets.

In a particular arrangement, the plant comprises at least one photobioreactor according to the invention for growing microorganisms and more than one photobioreactors for bioconversion, the growing photobioreactor(s) and the bioconverting photobioreactor(s) being arranged in series and wherein the photobioreactors for bioconversion are arranged in parallel with each other. Each photobioreactor for bioconversion is fed with a portion of the harvested material from an outflow line 38 from the said at least one growing photobioreactor.

The operation of this arrangement in series in continuous or semi-continuous mode enhances the overall yield of the photobioreactor system in optimizing culture conditions for each development stage and in continuously providing mature material to be further processed.

In an alternative arrangement in series, a plant may comprise more than one photobioreactor according to the invention for culturing microorganisms in series wherein each photobioreactor maintains the microorganisms in a specific phase of the life cycle (same or different) and wherein the carbon dioxide vented through the venting outlet 51 from the first photobioreactor is fed into a gas feeding chamber portion 60 of the same or a further photobioreactor through the lower feeding port 15. The operation of this arrangement in series in continuous or semi-continuous mode enhances the overall yield of the bioreactor system by optimizing the conversion efficiency of feeding $CO_2$ and decreasing the overall $CO_2$ efflux from the production plant.

According to an embodiment, the produced $O_2$ vented through the venting outlet 51 is advantageously captured and recycled for example in an oxy-fired burners (e.g. oxy-firing of coal in power plants) for further reducing $CO_2$ emissions, or upstream in a gas-feed preparation unit for eliminating poisons from the gas-feed.

According to another aspect, the invention provides a plant for growing and/or bioconverting photosynthesizing biomass comprising at least one photobioreactor according to the invention.

According to another aspect, the invention provides a method for growing photosynthesizing biomass on a continuous or semi continuous mode comprising:
(i) providing a photosynthesizing culture in an aqueous culture medium into a temperature-regulated culture chamber portion;
(ii) feeding the photosynthesizing culture with nutrients;
(iii) mixing and concentrating the said photosynthesizing culture into a culture concentrating zone from the said culture chamber portion;
(iv) homogeneously providing nutrient gas to the photosynthesizing culture medium;
(v) homogeneously providing a controlled light exposure to the said photosynthesizing culture in the concentrating zone from inside the culture medium;
(vi) continuously or semi-continuously harvesting a biomass from the said photosynthesizing culture.

In a further embodiment, the invention provides a method according to the invention wherein the nutrient gas is provided to the photosynthesizing culture medium inside the culture concentrating zone from the said culture chamber portion.

In a further embodiment, the invention provides a method according to the invention wherein the harvesting of the biomass is performed in or at the bottom of the culture concentrating zone from the said culture chamber portion.

In a further embodiment, the invention provides a method according to the invention wherein the homogeneous controlled light exposure provided under step (v) is achieved by providing inside the culture concentrating zone a controlled lighting system comprising a light source holder mounted on a rotating support having a rotation axis essentially parallel to the culture chamber portion axis and comprising a plurality of light sources.

In a further embodiment, the invention provides a method according to the invention wherein the homogeneous provision of nutrient gas to the photosynthesizing culture medium under step (vi) is achieved by providing to the culture concentrating zone a controlled gas feeding system comprising a gas bubble distribution platform comprising a gas gate formed of gas passages and a gas flow regulator.

In a further embodiment, the invention provides a method according to the invention wherein the method comprises a further step (vii) of monitoring independently a representative value of at least one parameter of the culture medium selected from temperature, pH, gas pressure, nutrient concentration, cell density and cell size and a further step (viii) of comparing the said representative value with a predetermined reference value to and a further step (ix) of adjusting at least one parameter of the culture medium selected from temperature, pH, gas flow, pressure, nutrient concentration, lighting (wavelength, intensity, lighting time, lighting cycle), feeding, concentrating and harvesting fluxes based on the result of the said comparison.

LIST OF ELEMENTS REFERENCED IN THE FIGURES

Continuous flow bioreactor
2 Housing (air-tight, essentially cylindrical)
  58 Interior chamber
    8 Culture chamber portion
      18 Culture concentrating zone
      19 Culture harvesting zone
      43 Gas collecting zone
    60 Gas feeding chamber portion
  59 Walls (59*a* side, 59*b* floor, 59*c* top)
    13 Upper feeding port
      14*a* valve
    15 Lower feeding port
      14*d* valve
    16 Control port
      14*b* valve
    17 Outflow port
      14*c* valve
    51 Venting outlet
      14*e* valve
    54 Overflow outlet
      14*f* valve
9 Temperature regulation system
  10 Temperature sensing element
  61 Heating/cooling member
    46 Internal envelope
      71 thermal fluid inlet
      72 thermal fluid outlet 12 Gas feeding system
   21 Gas bubble distribution platform
      40 Gas gate
         41 Gas passages
         45 Gas flow regulator
            28a Rotating support
            57a Drive
   22 Gas pressure regulation device
3 Flow-regulating system
   23 Culture mixing and concentrating entity
      47 Biomass-directing flow propulsion device
         44 Blades
         28b Rotating support
         57b Drive
4 Feeding device
   24 Upper feeding line
      35 Multiport valve
      54a Pump
   25 Lower feeding line
      54b Pump
5 Lighting system
   26 Light source holder device
      29 Light source holder
      30 Light source
   27 Light controlling unit
   28c Rotating support
      57c Drive
6 Feedback-control unit
   31 Sample collection unit
      42 Pump
   32 Control line
   33 Sample analyser
      50 Sensors
      51 Computer data acquisition system
   34 Multiport valve actuator
   36 Sample reinjection line
   37 Control device
7 Harvesting system
   38 outflow line
      54c Pump
   56 Harvesting reservoir
67 Gas collector system
   68 Venting gas line
69 Overflow collector system
   70 Overflow line
   53 Overflow sensor

The invention claimed is:

1. A photobioreactor for continuous or semi-continuous flow culturing photosynthesizing biomass, the photobioreactor including a housing (2) defining an interior chamber (58) comprising a culture chamber portion (8) and a gas feeding chamber portion (60), a temperature regulation system (9), a flow-regulating system (3) comprising a culture mixing and concentrating entity (23) comprising a biomass-directing flow propulsion device (47) and a lighting system (5), the culture chamber portion comprising a culture concentrating zone (18) and a culture harvesting zone (19) which is below the culture concentration zone, the temperature regulation system, the flow-regulating system being within the culture chamber portion, the lighting system being within the culture concentrating zone and the biomass-directing flow propulsion device causing an at least partially vertical flow of culture medium contained in the housing such that the biomass is concentrated in the culture concentrating zone and wherein the culture harvesting zone is located near the bottom end of the culture chamber (8) and further comprising a feed-back control unit (6) comprising a sample collection unit (31) and wherein feed-back control unit (6) further comprises a sample reinjection line (36) in fluid communication with an upper feeding line (24) of a feeding device (4) through the opening of a multiport valve (35) for re-injecting the sample collected in the sample collection unit (31) into the culture chamber portion (8).

2. The photobioreactor according to claim 1, further comprising a gas feeding system (12) and a harvesting system (7), wherein the gas feeding system (12) is at the bottom end of the culture concentrating zone (18).

3. The photobioreactor according to claim 1, wherein the lighting system (5) comprises a light source holder device (26), a light controlling unit (27) and a rotating support (28c) having a drive (57c).

4. The photobioreactor according to claim 3, wherein the light source holder device (26) comprises at least one light source holder (29) and a plurality of light sources (30) mounted on the light source holder such that the light sources are arranged essentially parallel to the axis of the photobioreactor and are substantially evenly distributed within the culture concentrating zone (18).

5. The photobioreactor according to claim 3, wherein the light sources (30) are spaced within the culture concentrating zone (18) at a distance which is less than or equal to the distance beyond which the photosynthesizing energy of the light source is sufficient to generate effective photosynthesis (Dmax).

6. The photobioreactor according to claim 3, wherein the light sources (30) are spaced within a plane perpendicular to the axis of the photobioreactor such that the element of volume within the concentration zone (18) receives essentially the same illumination duration and intensity independently from its distance from the axis of rotation of the lighting system (5).

7. The photobioreactor according to claim 2, wherein the gas feeding system 12 comprises a gas bubble distribution platform (21) comprising a gas gate (40) and a gas pressure regulation device (22).

8. The photobioreactor according to claim 7, wherein the gas gate comprises gas passages (41) and a gas flow regulator (45).

9. The photobioreactor according to claim 1, wherein the biomass-directing flow propulsion device (47) comprises blades (44) mounted on a rotating support (28b) having a drive (57b).

10. The photobioreactor according to claim 1, wherein the feed-back control unit (6) comprises a sample collection unit (31), a sample analyzer (33) and a control device (37).

11. The photobioreactor according to claim 10, wherein the sample analyzer (33) comprises at least one sensor (50) to analyze the culture sample and a computer acquisition system (51).

12. A production plant comprising at least one photobioreactor according to claim 1.

13. The production plant according to claim 12 comprising at least one photobioreactor according to claim 13 for growing microorganisms and more than one photobioreactors according to claim 13 for bioconversion, the growing photobioreactor(s) and the bioconverting photobioreactor(s) being arranged in series and wherein the photobioreactors for bioconversion are arranged in parallel with each other.

14. The production plant according to claim 13, wherein each photobioreactor for bioconversion is fed with a portion of the harvested material from an outflow line (38) from the said at least one growing photobioreactor.

15. The production plant according to claim 12 comprising more than one photobioreactor for culturing microorganisms in series wherein each photobioreactor maintains the microorganisms in a specific phase of the life cycle and wherein the walls (59*a*) or (59*c*) in the upper part of the housing (2), in the gas collecting zone (43) above the surface of the liquid medium in the culture chamber portion (8) further comprises a venting outlet (51) in fluid communication with the exterior of the photobioreactor through the aperture of a valve (14*e*) and the carbon dioxide vented through the venting outlet (51) from the first photobioreactor is fed into a gas feeding chamber portion (60) of the same or a further photobioreactor through the lower feeding port (15).

16. A method for growing photosynthesizing biomass on a continuous or semi continuous mode comprising:
   (i) introducing a photosynthesizing culture in an aqueous culture medium into a photobioreactor according to claim 1;
   (ii) feeding the photosynthesizing culture with nutrients;
   (iii) mixing and concentrating the said photosynthesizing culture into a culture concentrating zone of said photobioreactor;
   (iv) homogeneously providing nutrient gas to the photosynthesizing culture medium;
   (v) homogeneously providing a controlled light exposure to the said photosynthesizing culture in the concentrating zone from inside the culture medium; and
   (vi) continuously or semi-continuously harvesting a biomass from the said photosynthesizing culture.

17. The photobioreactor according to claim 1, wherein the interior chamber (58) is enclosed by bioreactor housing (59) comprising side, floor and top walls (59*a*), (59*b*), (59*c*) connected to at least one upper feeding port (13) closable by a valve (14*a*), at least one lower feeding port (15) closable by a valve (14*d*) in fluid communication with the gas feeding chamber portion (60) and at least one outflow port (17) at the level of the culture harvesting zone (19) and closable by a valve (14*c*) and wherein the walls (59*a*) or (59*c*) in the upper part of the housing (2), in the gas collecting zone (43) above the surface of the liquid medium in the culture chamber portion (8) further comprise a venting outlet (51) in fluid communication with the exterior of the photobioreactor through the aperture of a valve (14*e*).

* * * * *